United States Patent
Kamei et al.

(10) Patent No.: US 12,082,967 B2
(45) Date of Patent: Sep. 10, 2024

(54) RADIATION IMAGING SYSTEM

(71) Applicant: CANON KABUSHIKI KAISHA, Tokyo (JP)

(72) Inventors: Satoshi Kamei, Tokyo (JP); Shimpei Tezuka, Tochigi (JP); Kazuaki Umekawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 245 days.

(21) Appl. No.: 17/649,433

(22) Filed: Jan. 31, 2022

(65) Prior Publication Data
US 2022/0257208 A1 Aug. 18, 2022

(30) Foreign Application Priority Data

Feb. 12, 2021 (JP) .................................. 2021-021262
Dec. 7, 2021 (JP) .................................. 2021-198700

(51) Int. Cl.
*A61B 6/00* (2024.01)
*A61B 6/42* (2024.01)
(Continued)

(52) U.S. Cl.
CPC .......... *A61B 6/5258* (2013.01); *A61B 6/4233* (2013.01); *A61B 6/461* (2013.01);
(Continued)

(58) Field of Classification Search
CPC ...... H04N 5/321; H04N 25/671; H04N 25/40; H04N 5/32; H04N 25/63; H04N 5/341;
(Continued)

(56) References Cited

U.S. PATENT DOCUMENTS 9,395,450 B2   7/2016   Tezuka
10,422,893 B2   9/2019   Kamei
(Continued)

FOREIGN PATENT DOCUMENTS

JP   2008-154893 A   7/2008

OTHER PUBLICATIONS

U.S. Appl. No. 17/648,318, Kazuaki Umekawa, filed Jan. 19, 2022.
U.S. Appl. No. 17/648,593, Ryo Ezure, filed Jan. 21, 2022.

*Primary Examiner* — Irakli Kiknadze
(74) *Attorney, Agent, or Firm* — VENABLE LLP (57) ABSTRACT

A radiation imaging system comprising a radiation imaging apparatus in which pixels are arranged, a radiation source, a display unit, and a controller is provided. The controller causes, during radiation irradiation, the radiation imaging apparatus to repeat a generation operation of generating one image data by causing the pixels to perform an accumulating operation and a readout operation. When it is instructed to terminate the radiation irradiation, the controller causes the radiation source to stop the radiation irradiation in accordance with completion of the accumulating operation and the readout operation of the last row in the generation operation during which it was instructed to terminate the radiation irradiation, and causes the display unit to display an image based on last image data generated by the generation operation during which it was instructed to terminate the radiation irradiation.

14 Claims, 8 Drawing Sheets

(51) Int. Cl.
*A61B 6/46* (2024.01)
*G01N 23/04* (2018.01)

(52) U.S. Cl.
CPC ............... *A61B 6/487* (2013.01); *A61B 6/54* (2013.01); *G01N 23/04* (2013.01); *G01N 2223/406* (2013.01)

(58) Field of Classification Search
CPC .... H04N 5/361; H04N 5/3651; A61B 6/4233; A61B 6/54; A61B 6/5258; A61B 6/461; A61B 6/487; A61B 6/467; A61B 6/405; A61B 6/46; A61B 6/40; A61B 6/4014; A61B 6/06; A61B 6/4035; A61B 6/469; A61B 6/542; A61B 6/465; A61B 6/0407; A61B 6/4435; A61B 6/4441; A61B 6/485; A61B 6/545; A61B 6/488; A61B 6/587; A61B 6/5294; A61B 6/544; A61B 6/4447; A61B 2034/2055; A61B 6/4405; A61B 6/4476; A61B 6/547; A61B 2090/376; A61B 6/5211; A61B 6/52; A61B 6/585; A61B 6/504; A61B 6/463; A61B 6/56; A61B 6/582; A61B 6/5264; A61B 6/4283; A61B 6/5235; A61B 6/5241; G01N 23/04; G01N 2223/406; G01N 2223/303; G21K 1/046; G21K 1/025; G21K 1/04; G16H 40/63; G16H 50/20; G06T 7/33; G06T 2207/10016; G06T 2207/10116; G01T 1/17; G01T 1/2018
USPC .......................................................... 378/62
See application file for complete search history.

(56) References Cited

U.S. PATENT DOCUMENTS

| | | |
|---|---|---|
| 10,498,975 B2 | 12/2019 | Tezuka et al. |
| 10,856,834 B2 | 12/2020 | Uchiyama et al. |
| 11,079,341 B2 | 8/2021 | Tezuka |
| 11,153,511 B2 | 10/2021 | Tezuka et al. |
| 2014/0341350 A1 | 11/2014 | Muroi |
| 2018/0064955 A1 | 3/2018 | Iseki |
| 2018/0067215 A1* | 3/2018 | Mako ..................... G01T 1/247 |
| 2020/0253569 A1 | 8/2020 | Kobayashi |

* cited by examiner

RADIATION IMAGING SYSTEM

BACKGROUND OF THE INVENTION

Field of the Invention

The present invention relates to a radiation imaging system.

Description of the Related Art

In medical image diagnosis and nondestructive inspection, a radiation imaging apparatus using an FPD (Flat Panel Detector) made of a semiconductor material is widely used. The radiation imaging apparatus is used for fluoroscopic imaging to capture a moving image. Japanese Patent Laid-Open No. 2008-154893 discloses an X-ray imaging apparatus that has a last image hold function in which, when fluoroscopic imaging is interrupted, the last image in the fluoroscopic imaging is displayed on a monitor.

SUMMARY OF THE INVENTION

When executing fluoroscopic imaging while using an FPD of line exposure sequential readout type, which accumulates signals and reads out signals for each row, and performing continuous radiation irradiation, the accumulation time from the start of signal accumulation to the end of irradiation can change for each row at the time of termination of the radiation irradiation. If the signal accumulation time change for each row, shading may occur in a last image obtained at the time of termination of the radiation irradiation.

Some embodiments of the present invention provide a technique advantageous in, in a radiation imaging system having a last image hold function, improving the quality of an image displayed when fluoroscopic imaging is interrupted.

According to some embodiments, a radiation imaging system comprising a radiation imaging apparatus in which a plurality of pixels are arranged in a matrix to acquire a radiation image, a radiation source configured to continuously irradiate the radiation imaging apparatus with radiation, a display unit, and a controller configured to control an operation of the radiation imaging apparatus, wherein the controller is configured to cause, during radiation irradiation, the radiation imaging apparatus to repeat a generation operation of generating one image data by causing the plurality of pixels to perform an accumulating operation and a readout operation at least row by row from a first row to a last row, and when it is instructed to terminate the radiation irradiation, the controller is configured to cause the radiation source to stop the radiation irradiation in accordance with completion of the accumulating operation and the readout operation of the last row in, among the generation operations, the generation operation during which it was instructed to terminate the radiation irradiation, and cause the display unit to display an image based on last image data generated by, among the generation operations, the generation operation during which it was instructed to terminate the radiation irradiation, is provided.

According to some other embodiments, a radiation imaging system comprising a radiation imaging apparatus in which a plurality of pixels are arranged in a matrix to acquire a radiation image, a radiation source configured to continuously irradiate the radiation imaging apparatus with radiation, a display unit, and a controller configured to control an operation of the radiation imaging apparatus, wherein the controller is configured to cause, during radiation irradiation, the radiation imaging apparatus to repeat a generation operation of generating one image data by causing the plurality of pixels to perform an accumulating operation and a readout operation at least row by row from a first row to a last row, and when it is instructed to terminate the radiation irradiation, the controller is configured to cause the radiation source to stop the radiation irradiation, and cause the display unit to display an image based on last image data generated by, among the generation operations, the generation operation at least one before the generation operation during which it was instructed to terminate the radiation irradiation, is provided.

According to still other embodiments, a radiation imaging system comprising a radiation imaging apparatus in which a plurality of pixels are arranged in a matrix to acquire a radiation image, a radiation source configured to continuously irradiate the radiation imaging apparatus with radiation, a display unit, and a controller configured to control an operation of the radiation imaging apparatus, wherein the controller is configured to cause, during radiation irradiation, the radiation imaging apparatus to repeat a generation operation of generating one image data by causing the plurality of pixels to perform an accumulating operation and a readout operation at least row by row from a first row to a last row, and when it is instructed to terminate the radiation irradiation, the controller is configured to causes the radiation imaging apparatus to operate by selecting one of a first terminating operation in which the radiation source is caused to stop the radiation irradiation in accordance with completion of the accumulating operation and the readout operation of the last row in, among the generation operations, the generation operation during which it was instructed to terminate the radiation irradiation, and the display unit is caused to display an image based on last image data generated by, among the generation operations, the generation operation during which it was instructed to terminate the radiation irradiation, and a second terminating operation in which the radiation source is caused to stop the radiation irradiation, and the display unit is caused to display an image based on last image data generated by, among the generation operations, the generation operation at least one before the generation operation during which it was instructed to terminate the radiation irradiation, is provided.

According to yet other embodiments, a radiation imaging system comprising a radiation imaging apparatus in which a plurality of pixels are arranged in a matrix to acquire a radiation image, a radiation source configured to continuously irradiate the radiation imaging apparatus with radiation, a display unit, and a controller configured to control an operation of the radiation imaging apparatus, wherein the controller is configured to causes, during radiation irradiation, the radiation imaging apparatus to repeat a generation operation of generating one image data by causing the plurality of pixels to perform an accumulating operation and a readout operation at least row by row from a first row in a region of interest, which is set in advance with respect to the plurality of pixels arranged in the matrix, to a last row in the region of interest, and when it is instructed to terminate the radiation irradiation, the controller is configured to cause the radiation source to stop the radiation irradiation in accordance with completion of the accumulating operation and the readout operation of the last row in the region of interest in, among the generation operations, the generation operation during which it was instructed to terminate the radiation irradiation, and cause the display unit to display an image based on last image data generated by, among the generation operations, the generation operation during which it was instructed to terminate the radiation irradiation, is provided.

According to further embodiments, a radiation imaging system comprising a radiation imaging apparatus in which a plurality of pixels are arranged in a matrix to acquire a radiation image, a radiation source configured to continuously irradiate the radiation imaging apparatus with radiation, a display unit, and a controller configured to control an operation of the radiation imaging apparatus, wherein the controller is configured to cause, during radiation irradiation, the radiation imaging apparatus to repeat a generation operation of generating one image data by causing the plurality of pixels to perform an accumulating operation and a readout operation at least row by row from a first row in a region of interest, which is set in advance with respect to the plurality of pixels arranged in the matrix, to a last row in the region of interest, and when it is instructed to terminate the radiation irradiation, the controller is configured to cause the radiation imaging apparatus to operate by selecting one of a first terminating operation in which the radiation source is caused to stop the radiation irradiation in accordance with completion of the accumulating operation and the readout operation of the last row in the region of interest in, among the generation operations, the generation operation during which it was instructed to terminate the radiation irradiation, and the display unit is caused to display an image based on last image data generated by, among the generation operations, the generation operation during which it was instructed to terminate the radiation irradiation, and a second terminating operation in which the radiation source is caused to stop the radiation irradiation, and the display unit is caused to display an image based on last image data generated by, among the generation operations, the generation operation at least one before the generation operation during which it was instructed to terminate the radiation irradiation, is provided.

Further features of the present invention will become apparent from the following description of exemplary embodiments (with reference to the attached drawings).

DESCRIPTION OF THE EMBODIMENTS

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation in the present invention can include $\alpha$-rays, $\beta$-rays, $\gamma$-rays, and the like which are beams generated by particles (including photons) emitted by radiation decay, as well as beams having the similar or higher energy, for example, X-rays, particle beams, cosmic rays, and the like.

Figure 1:
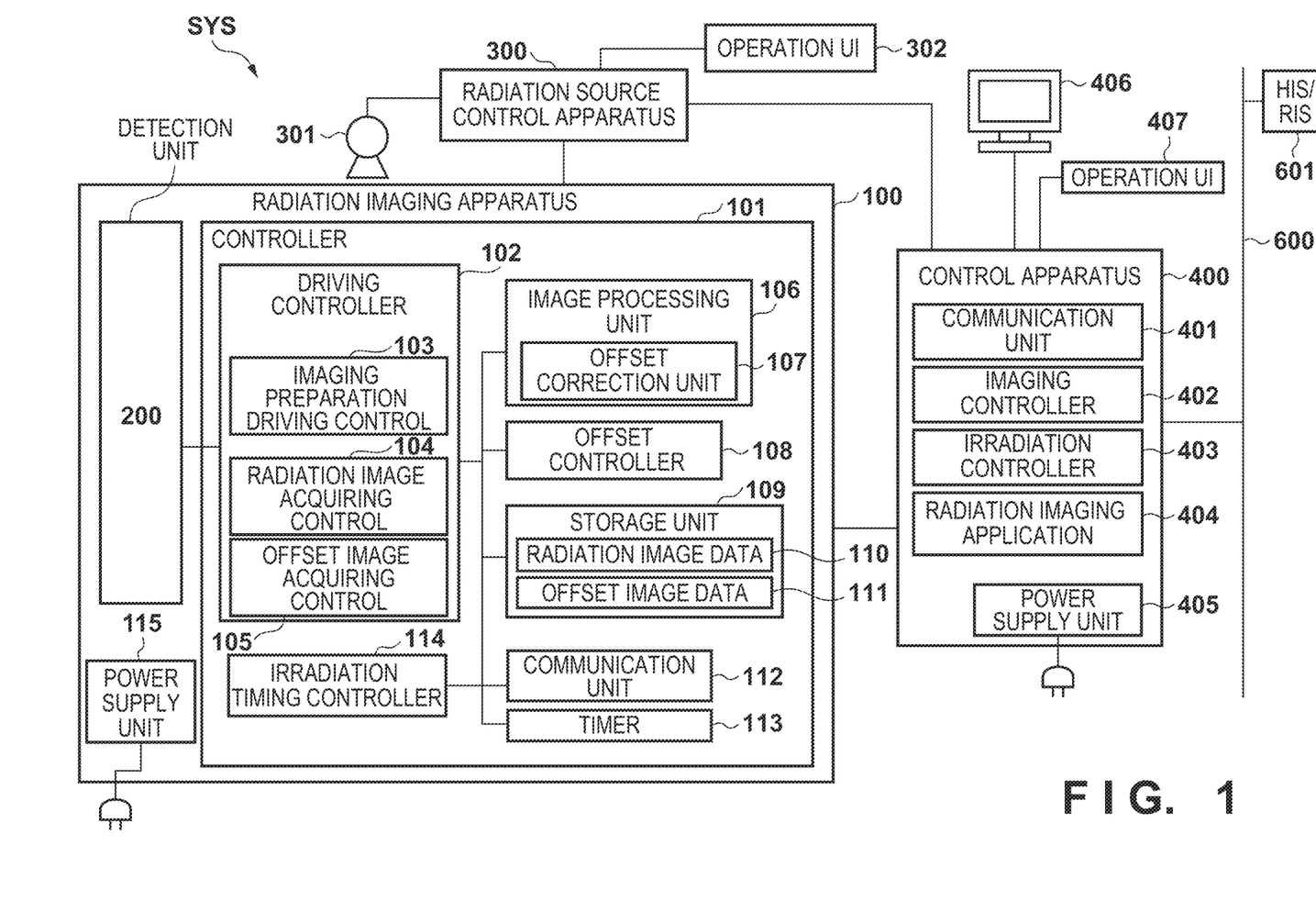
FIG. 1 is a block diagram showing a configuration example of a radiation imaging system according to an embodiment.

With reference to FIGS. 1 to 8, the configuration and operation of a radiation imaging system according to this embodiment will be described. FIG. 1 is a block diagram showing a configuration example of a radiation imaging system SYS according to this embodiment. The radiation imaging system SYS according to this embodiment can be used for, for example, medical purposes.

The radiation imaging system SYS includes a radiation imaging apparatus 100, a radiation source 301, and a control apparatus 400 including a display unit 406. The radiation imaging apparatus 100 includes a detection unit 200 in which a plurality of pixels used to acquire a radiation image corresponding to incident radiation are arranged in a matrix. The radiation source 301 is controlled by a radiation source control apparatus 300, and irradiates the radiation imaging apparatus 100 with radiation. The control apparatus 400 controls the radiation imaging apparatus 100 and the radiation source control apparatus 300. The control apparatus 400 communicates control signals with the radiation imaging apparatus 100 to collect radiation image data from the radiation imaging apparatus 100 and display a radiation image based on the radiation image data. Further, the control apparatus 400 includes a radiation imaging application 404 that can accept an imaging order and register imaging information for generating a control signal including the imaging mode for acquiring a radiation image by the detection unit 200.

The control apparatus 400 is connected to an in-hospital network 600 formed by, for example, a LAN (Local Area Network). An HIS (Hospital Information System)/RIS (Radiology Information System) 601 is connected to the in-hospital network 600. The control apparatus 400 and the HIS/RIS 601 can communicate with each other and exchange, for example, the imaging order of a radiation image, imaging information including patient information, and radiation image data in the hospital.

The radiation imaging apparatus 100 includes the detection unit 200, a controller 101, and a power supply unit 115. The detection unit detects the radiation entering the detection unit 200, and generates image data corresponding to the dose of the detected radiation. The controller 101 controls respective components arranged in the radiation imaging apparatus 100. The controller 101 includes a driving controller 102, an image processing unit 106, an offset controller 108, a storage unit 109, a communication unit 112, a timer 113, and an irradiation timing controller 114. The driving controller 102 controls the operation of the detection unit 200 so as to acquire radiation image data corresponding to radiation irradiation and offset image data used to correct the radiation image data. The image processing unit 106 performs image processing on image data acquired from the detection unit 200. The offset controller 108 controls the timing of updating an offset image. The storage unit 109 stores acquired image data. The communication unit 112 controls the communication with the control apparatus 400 and the communication with the radiation source control apparatus 300. For example, the communication unit 112 receives, from the control apparatus 400, a control signal including the imaging mode for acquiring a radiation image by the detection unit 200. The timer 113 acquires an imaging time, an elapse time, and the like. The irradiation timing controller 114 controls transition to the imaging operation of the detection unit 200 in accordance with a radiation irradiation signal from the radiation source control apparatus 300 to the radiation source 301. The power supply unit 115 supplies power to the respective components in the radiation imaging apparatus 100.

For example, the controller 101 may read out a program stored in the storage unit 109 and control the entire radiation imaging apparatus 100 based on the readout program. Further, the controller 101 may include a control signal generation circuit such as an ASIC and control the radiation imaging apparatus 100. Furthermore, control of the entire radiation imaging apparatus 100 may be implemented by both the program and the control signal generation circuit.

The driving controller 102 controls the detection unit 200 by switching a plurality of control modes including imaging preparation driving control 103, radiation image acquiring control 104, and offset image acquiring control 105. The imaging preparation driving control 103 is control for preparing the detection unit 200 in a state in which a radiation image can be captured. The radiation image acquiring control 104 is control for driving the detection unit 200 so as to acquire radiation image data. The offset image acquiring control 105 is control for driving the detection unit 200 so as to acquire offset image data. In the imaging preparation driving control 103, the driving controller 102 causes the detection unit 200 to periodically read out electric charges while applying a voltage similar to that upon imaging, so that dark charges accumulated in the respective pixels arranged in the detection unit 200 are reset. The signal read out from the pixel at this time is not handled as image data so may not be stored in the storage unit 109. In the radiation image acquiring control 104, the driving controller 102 drives the detection unit 200 as in the imaging preparation driving control 103, so that electric charges corresponding to radiation irradiation are accumulated in the pixels arranged in the detection unit 200. Then, the electric charges accumulated in the pixels are read out as radiation image data 110 and stored in the storage unit 109. A moving image can be captured by the driving controller 102 continuously performing the radiation image acquiring control 104. In the offset image acquiring control 105, the driving controller 102 drives the detection unit 200 as in the imaging preparation driving control 103, and stores image data, which is read out in a state in which no radiation irradiation is performed, as offset image data 111 in the storage unit 109.

On the radiation image data 110 acquired from the detection unit 200 by the radiation image acquiring control 104, offset correction is performed using the offset image data 111 acquired in advance by the offset image acquiring control 105. The processing of offset correction may be performed by an offset correction unit 107 of the image processing unit 106. The radiation image data having undergone the offset correction is transferred to the control apparatus 400 via the communication unit 112. Although only the processing of offset correction is described here, the image processing unit 106 may perform another correction processing such as defective pixel correction or gain correction of correcting the gain variation of the amplifier arranged in the detection unit 200. Alternatively, the correction processing as described above may not be performed in the radiation imaging apparatus 100. For example, the acquired radiation image data 110 and offset image data 111 may be transferred to the control apparatus 400 without undergoing the correction processing or the like, and the control apparatus 400 may perform the correction processing as described above. As the offset image data used for offset correction, for example, image data generated by acquiring a plurality of offset image data and performing noise component reduction processing by averaging or the like may be used.

The radiation source control apparatus 300 includes an operation UI 302 used to operate the radiation source control apparatus 300. The operation UI 302 can include a keyboard, a mouse, an exposure switch, and the like. A user may set a radiation irradiation condition or perform radiation irradiation using the operation UI 302. The radiation source control apparatus 300 and the radiation imaging apparatus 100 can exchange information using a dedicated signal line. The radiation source control apparatus 300 and the radiation imaging apparatus 100 may exchange, for example, synchronization signals such as a notification of the start or end of radiation irradiation and a notification of the radiation irradiation enable timing. With this, the radiation imaging apparatus 100 and the radiation source 301 controlled by the radiation source control apparatus 300 are configured to be capable of capturing a radiation image without intervention of the control apparatus 400.

The control apparatus 400 includes an imaging controller 402, an irradiation controller 403, a communication unit 401, the radiation imaging application 404, the display unit 406, an operation UI 407, and a power supply unit 405, and controls the respective components of the radiation imaging system SYS. The imaging controller 402 controls, in accordance with the user setting received via the radiation imaging application 404, the radiation imaging apparatus 100 to control the timing of acquiring image data, set the imaging conditions including the imaging mode for acquiring a radiation image by the detection unit 200, and the like. The irradiation controller 403 controls, in accordance with the user setting received via the radiation imaging application 404, the irradiation condition of radiation applied form the radiation source 301 by controlling the radiation source control apparatus 300. The communication unit 401 controls the communication with the radiation imaging apparatus 100, the radiation source control apparatus 300, and the in-hospital network 600. The radiation imaging application 404 accepts the imaging order and registers the imaging information. The display unit 406 displays a radiation image based on radiation image data acquired by the radiation imaging apparatus 100 or the information of an imaging condition such as the imaging mode for performing imaging. The operation UI 407 can be a mouse or keyboard used to operate the radiation imaging application 404. The power supply unit 405 supplies power to the respective components in the control apparatus 400.

Here, the communication between the control apparatus 400 and the radiation imaging apparatus 100 and the communication between the control apparatus 400 and the radiation source control apparatus 300 may be cable connection communication using a standard such as RS232C, USB, or Ethernet. Further, the communication between the control apparatus 400 and the radiation imaging apparatus 100 and the communication between the control apparatus 400 and the radiation source control apparatus 300 may be communication using a dedicated signal line, or may be wireless communication. Furthermore, the communication between the control apparatus 400 and the radiation imaging apparatus 100 and the communication between the control apparatus 400 and the radiation source control apparatus 300 may be a combination of wired communication and wireless communication.

In the communication between the control apparatus 400 and the radiation imaging apparatus 100, for example, image data and a signal indicating the apparatus status of the radiation imaging apparatus 100 are transmitted from the radiation imaging apparatus 100 to the control apparatus 400. Further, for example, a control signal including a signal indicating the condition setting such as the imaging mode for acquiring image data is transmitted from the control apparatus 400 to the radiation imaging apparatus 100. In the communication between the control apparatus 400 and the radiation source control apparatus 300, for example, a signal indicating the setting of a radiation irradiation condition and the like are transmitted from the control apparatus 400 to the radiation source control apparatus 300. Further, for example, a signal indicating the apparatus status of the radiation source control apparatus 300 and a signal indicating the actual irradiation information at the time of radiation irradiation are transmitted from the radiation source control apparatus 300 to the control apparatus 400.

Figure 2:
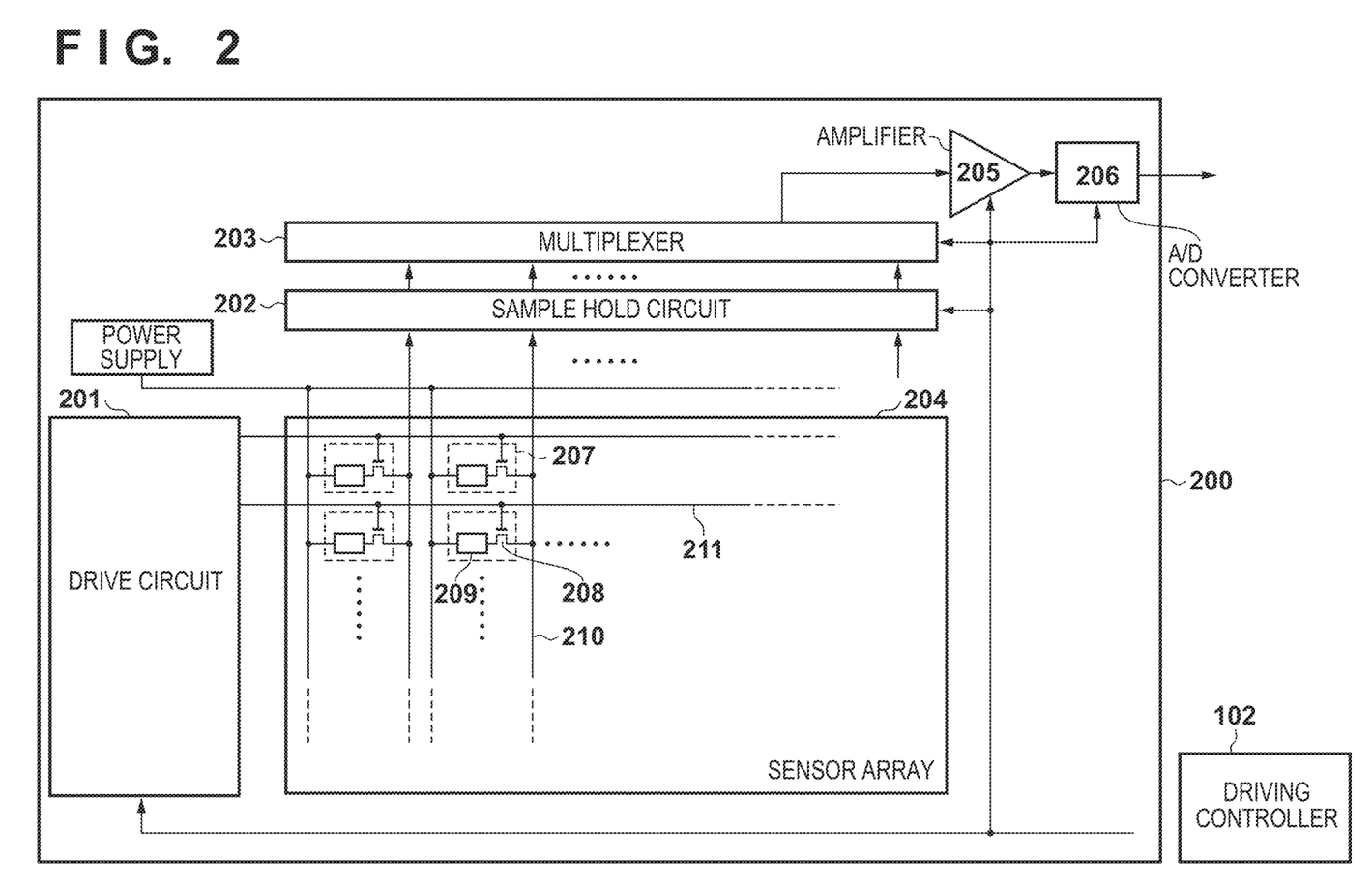
FIG. 2 is a block diagram showing an arrangement example of a detection unit of the radiation imaging system shown in FIG. 1.

FIG. 2 is a block diagram showing an arrangement example of the detection unit 200 of the radiation imaging apparatus 100. The detection unit 200 includes a sensor array 204 including a plurality of pixels 207 arrayed in a two-dimensional array so as to form a plurality of rows and a plurality of columns to acquire a radiation image corresponding to incident radiation. The pixel 207 arranged in the sensor array 204 includes, for example, a switch element 208 such as a TFT (Thin Film Transistor) and a photoelectric conversion element 209, and a scintillator (not shown) can be arranged on the pixel 207 (photoelectric conversion element 209). The scintillator can be integrally formed in the sensor array 204. If the pixel 207 includes the scintillator and the photoelectric conversion element 209, the radiation entering the detection unit 200 is converted into visible light by the scintillator, the converted visible light enters the photoelectric conversion element 209 of the pixel 207, and electric charges corresponding to the visible light are generated in the photoelectric conversion element 209. In this manner, a so-called indirect conversion type conversion element which converts the incident radiation into electric charges by the scintillator and the photoelectric conversion element 209 may be used as the pixel 207. Alternatively, for example, a so-called direct conversion type conversion element which is not provided with the scintillator and directly converts the incident radiation into electric charges may be used as the pixel 207. By switching the switch element 208 between the ON (conductive) state and the OFF (non-conductive) state, accumulation of the electric charges generated by the photoelectric conversion element 209 and readout of the electric charges are performed, and radiation image data can be acquired.

In the pixel 207 arranged in the sensor array 204 of the detection unit 200, the switch element 208 is set in the ON state when a voltage for setting the switch element 208 in the ON state is applied for each row from a drive circuit 201 via a common driving line 211. When the switch element 208 is set in the ON state, a signal corresponding to the electric charges accumulated in the pixel 207 is transferred to a sample hold circuit 202 via a signal line 210 connected to each pixel 207. After that, the signals output from the pixels 207 and held in the sample hold circuit 202 are sequentially read out via a multiplexer 203, amplified by an amplifier 205, and converted into digital value image data by an A/D converter 206. When a voltage for setting the switch element 208 in the OFF state is applied from the drive circuit 201 via the driving line 211, the pixel 207 in which readout of the electric charges is completed returns to a state of accumulating electric charges. In this manner, the drive circuit 201 sequentially scans the pixels 207 arranged on the sensor array 204 for each line, and signals finally output from all the pixels 207 are converted into a digital value. With this, the image data for generating a radiation image can be read out. Control for the above-described driving operation, readout operation, or the like of the detection unit 200 is performed by the driving controller 102 of the controller 101. The image data converted into the digital value may be, for example, temporarily stored in the storage unit 109 shown in FIG. 1.

Figure 3:
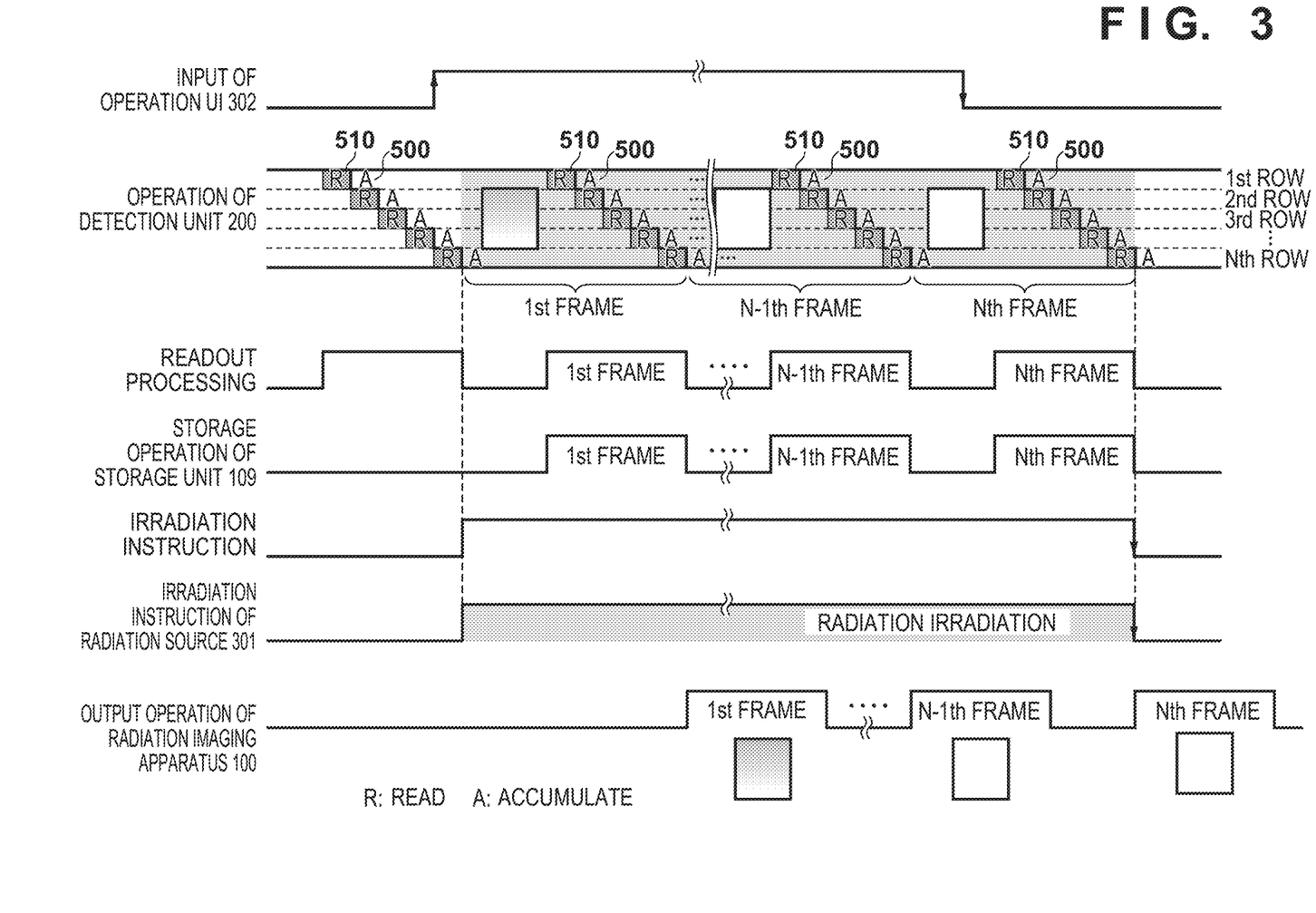
FIG. 3 is a timing chart for explaining an operation of the radiation imaging system shown in FIG. 1.

Next, an operation of the radiation imaging system SYS in this embodiment will be described. FIG. 3 is a timing chart showing an operation example of the radiation imaging system SYS in this embodiment. In this embodiment, in accordance with a user operation, the radiation source 301 continuously irradiate the radiation imaging apparatus 100 with radiation to capture a moving image (continuous fluoroscopy). When fluoroscopic imaging is interrupted or terminated, a last image hold operation of displaying the last image in the fluoroscopic imaging on the display unit 406 is performed. FIG. 3 shows a sequence of operations of the radiation imaging apparatus 100 and the radiation source 301 (radiation source control apparatus 300) in the continuous fluoroscopy.

"Operation UI 302 input" indicates a signal for the user to request capturing of a radiation image. In FIG. 3, for example, when the user presses an exposure switch for starting continuous fluoroscopy, "operation UI 302 input" changes to high level. "Detection unit 200 operation" indicates the operation state of the sensor array 204 of the detection unit 200. "Readout processing" indicates an operation of transferring image data from the detection unit 200 to the controller 101 in the radiation imaging apparatus 100. "Storage unit 109 storage operation" indicates an operation of storing, in the storage unit 109, the image data transferred to the controller 101. "Irradiation instruction" indicates a signal from the irradiation timing controller 114 instructing the radiation source control apparatus 300 to perform radiation irradiation. "Radiation source 301 irradiation instruction" indicates a signal from the radiation source control apparatus 300 instructing the radiation source 301 to perform radiation irradiation in accordance with "irradiation instruction". In FIG. 3, while "radiation source 301 irradiation instruction" is at high level, the radiation source 301 performs radiation irradiation. "Radiation imaging apparatus 100 output operation" indicates an operation of transferring image data from the radiation imaging apparatus 100 to the control apparatus 400.

Next, operations of the radiation imaging apparatus 100 and the radiation source 301 (radiation source control apparatus 300) in continuous fluoroscopy will be described. Before it is instructed by the user, via the operation UI 302, to start radiation irradiation, the control apparatus 400 causes the radiation imaging apparatus 100 to start a generation operation for generating image data. The generation operation is an operation of generating one image data by causing the detection unit 200 of the radiation imaging apparatus 100 to cause the plurality of pixels 207 to perform an accumulating operation 500 and a readout operation 510 at least row by row from the first row to the last row. By repeating the generation operation, a moving image can be captured.

As indicated by "detection unit 200 operation" and "readout processing", the accumulating operation 500 and the readout operation 510 are repeated prior to the start of radiation irradiation. This operation can be also referred to as reset driving for suppressing the influence of dark charges generated in the pixel 207 or the like. The signal read out from the pixel 207 at this time is not handled as image data so may not be stored in the storage unit 109.

Then, when it is instructed by the user to start radiation irradiation by pressing the exposure switch of the operation UI 302 or the like, the radiation imaging system SYS starts continuous fluoroscopy. When the readout operation 510 of the last row (shown as the Nth row in FIG. 3) of the plurality of pixels 207 arranged in the sensor array 204 is completed, the irradiation timing controller 114 transmits, to the radiation source control apparatus 300, a signal instructing to start radiation irradiation. The radiation source control apparatus 300, which has received the signal instructing to start radiation irradiation, instructs the radiation source 301 to perform radiation irradiation, and the radiation source 301 starts radiation irradiation. That is, when it is instructed to start radiation irradiation, the radiation source 301 is caused to start radiation irradiation in accordance with the completion of the readout operation 510 of the last row in, among the generation operations, the generation operation during which it was instructed to start irradiation radiation.

During radiation irradiation, the radiation imaging apparatus 100 repeats the above-described generation operation. By the generation operation, one image data is generated in one frame. The image data read out by the readout operation 510 is transferred to the controller 101 and stored as the radiation image data 110 in the storage unit 109. The image data stored as the radiation image data 110 in the storage unit 109 undergoes offset correction processing by the offset correction unit 107 using the offset image data 111 stored in the storage unit 109 in advance, and the processed image data is transferred to the control apparatus 400 via the communication unit 112. An image based on the image data transferred to the control apparatus 400 is displayed on the display unit 406. By repeating these operations, continuous fluoroscopy is executed.

As shown in FIG. 3, when generating the image data for the first frame, the radiation irradiation time in the accumulating operation 500 changes for each row. Therefore, shading can occur in the image generated from the image data for the first frame. On the other hand, after the second frame, the radiation irradiation time in the accumulating operation 500 does not change for each row, so that shading can be suppressed.

Next, a case will be described in which, for example, the user returns the exposure switch of the operation UI 302 in the Nth frame to interrupt or terminate the continuous fluoroscopy. When it is instructed to terminate the radiation irradiation, the irradiation timing controller 114 maintains the "irradiation instruction" signal at high level until the timing at which the readout operation 510 of the last row (Nth row) of the plurality of pixels 207 arranged in the sensor array 204 is completed in the Nth frame where the accumulating operation 500 has been already started. When the readout operations of all the rows in the Nth frame are completed, the "irradiation instruction" signal is changed to low level. In accordance with the change of the "irradiation instruction" signal to low level, the radiation source control apparatus 300 changes the "radiation source 301 irradiation instruction" signal output to the radiation source 301 to low level. Thus, the radiation source 301 stops the radiation irradiation in accordance with the completion of the accumulating operation 500 and the readout operation 510 of the last row in, among the generation operations, the generation operation in the Nth frame during which it was instructed to terminate the radiation irradiation.

Since the radiation irradiation is performed until the accumulating operation 500 and the readout operation 510 of the last row in the generation operation in the Nth frame are completed, the image data for the Nth frame during which it was instructed to terminate the radiation irradiation is data of the time at which the radiation irradiation times in the accumulating operations 500 are equal to each other for the respective rows. Further, the image data for the Nth frame can be data of the time at which the radiation irradiation times in the accumulating operations 500 are equal to each other for the respective rows. The control apparatus 400 causes the display unit 406 to display an image based on the last image data generated by the generation operation in the Nth frame during which it was instructed to terminate the radiation irradiation. Thus, it is possible to provide the radiation imaging system SYS that can obtain, even when the continuous fluoroscopy is terminated or interrupted, a clear image in which each of the plurality of pixels 207 arranged in the sensor array 204 is irradiated with radiation.

The operation shown in FIG. 3 shows that the accumulating operation 500 and the readout operation 510 are performed row by row from the first row to the Nth row (last row), but the present invention is not limited to this. For example, the accumulating operation 500 and the readout operation 510 may be performed for multiple rows such as for two rows or for three rows. Further, the radiation source 301 stops the radiation irradiation in accordance with the completion of the accumulating operation 500 and the readout operation 510 of the last row in the generation operation in the Nth frame, but the present invention is not limited to this. The radiation source 301 may stop the radiation irradiation in accordance with the completion of the accumulating operation 500 of the last row in the generation operation in the Nth frame. Even in this case, the radiation irradiation times in the accumulating operations 500 can be equal to each other for the respective rows.

After it is instructed to terminate the radiation irradiation, the control apparatus 400 causes the radiation imaging apparatus 100 to stop the generation operation in which the accumulating operation 500 and the readout operation 510 are performed. In this case, the control apparatus 400 may not cause the radiation imaging apparatus 100 to output, to the control apparatus 400, the image data generated by the generation operation performed after the generation operation in which the last image data was generated. Alternatively, in this case, the image data generated by the generation operation performed after the generation operation in which the last image data was generated may not be transferred from the detection unit 200 to the controller 101. Alternatively, for example, the image data generated by the generation operation performed after the generation operation in which the last image data was generated may not be stored in the storage unit 109. Since the image data generated by the generation operation performed after the generation operation in which the last image data was generated is not transferred to the storage unit 109 or the communication unit 112, it is not output from the radiation imaging apparatus 100.

For example, the image displayed on the display unit 406 after the radiation irradiation is terminated is not limited to an image based on the last image data alone. The control apparatus 400 may cause the display unit 406 to display an image based on a plurality of image data including the last image data generated in the Nth frame and the image data generated by the generation operation one before (in the (N−1)th frame) the generation operation in which the last image data was generated. A composite image based on the data generated by adding or averaging the plurality of image data can be displayed on the display unit 406. The incident radiation dose in fluoroscopy imaging is often smaller than in still image capturing. By generating an image based on a plurality of image data, noise components in the image displayed on the display unit 406 are suppressed, and the image quality can be improved.

Figure 4:
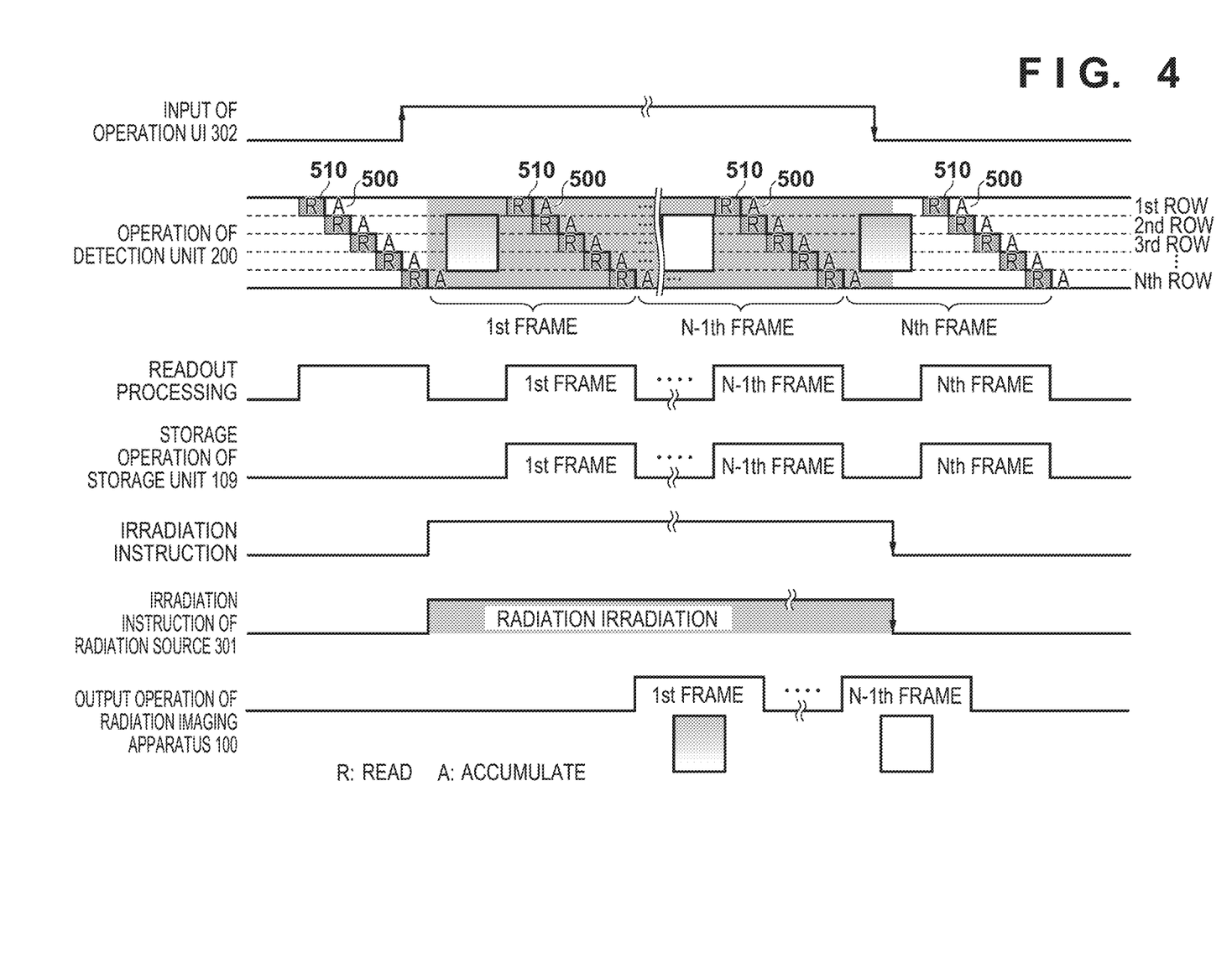
FIG. 4 is a timing chart for explaining another operation of the radiation imaging system shown in FIG. 1.

FIG. 4 is a timing chart showing a modification of the operations of the radiation imaging apparatus 100 and the radiation source 301 (radiation source control apparatus 300) in continuous fluoroscopy shown in FIG. 3. As in the operations shown in FIG. 3, FIG. 4 shows a case in which it is instructed to terminate the radiation irradiation in the Nth frame from the start of continuous fluoroscopy.

In the operations shown in FIG. 4, when an instruction to terminate the radiation irradiation is input, the irradiation timing controller 114 changes the "irradiation instruction" signal to low level. In accordance with the change of the "irradiation instruction" signal to low level, the radiation source control apparatus 300 changes the "radiation source 301 irradiation instruction" signal output to the radiation source 301 to low level. Thus, the radiation source 301 stops the radiation irradiation. Therefore, the image data for the Nth frame is data in which the radiation irradiation time in the accumulating operation 500 changes each row. Accordingly, when the display unit 406 displays an image based on the image data for the Nth frame, shading may occur in the displayed image.

To prevent this, the control apparatus 400 causes the display unit 406 to display an image based on the image data (last image data) generated by the generation operation in the (N−1)th frame one before the generation operation in the Nth frame during which it was instructed to terminate the radiation irradiation. That is, the image displayed on the display unit 406 is an image based on the image data of the time at which the radiation irradiation times in the accumulating operations 500 are equal to each other for the respective rows. Thus, also in the operation shown in FIG. 4, as in the operation shown in FIG. 3, it is possible to provide the radiation imaging system SYS that can obtain a clear image in which each of the plurality of pixels 207 arranged in the sensor array 204 is irradiated with radiation.

Also in the operation shown in FIG. 4, the image data generated by the generation operations (in the Nth and subsequent frames) performed after the generation operation in which the last image data was generated may not be transferred from the radiation imaging apparatus 100 to the control apparatus 400. Alternatively, the image data generated by the generation operations in the Nth and subsequent frames may not be transferred from the detection unit 200 to the controller 101, or may not be stored in the storage unit 109. The image to be displayed on the display unit 406 may be generated from the last image data and one or more image data generated by the generation operations in the frames before the frame in which the last image data was generated. Alternatively, the image to be displayed on the display unit 406 may be generated using the last image data and the image data generated by the generation operation in the frame two frames before the frame in which the last image data was generated. That is, the image to be displayed on the display unit 406 may be generated using the last image data and the image data generated by the generation operation in the frame at least one frame before the frame in which the last image data was generated.

When the exposure switch is released, the radiation imaging apparatus 100 may determine whether to extend the radiation irradiation by continuing the "irradiation instruction" signal until the timing at which the readout operation 510 of the last row (Nth row) in the Nth frame is completed as shown in FIG. 3, or to immediately stop the radiation irradiation as shown in FIG. 4, and switch the terminating operation of terminating (interrupting) the continuous fluoroscopy. An example of the terminating operation determination procedure in the continuous fluoroscopy in this case will be described with reference to FIG. 5.

Figure 5:
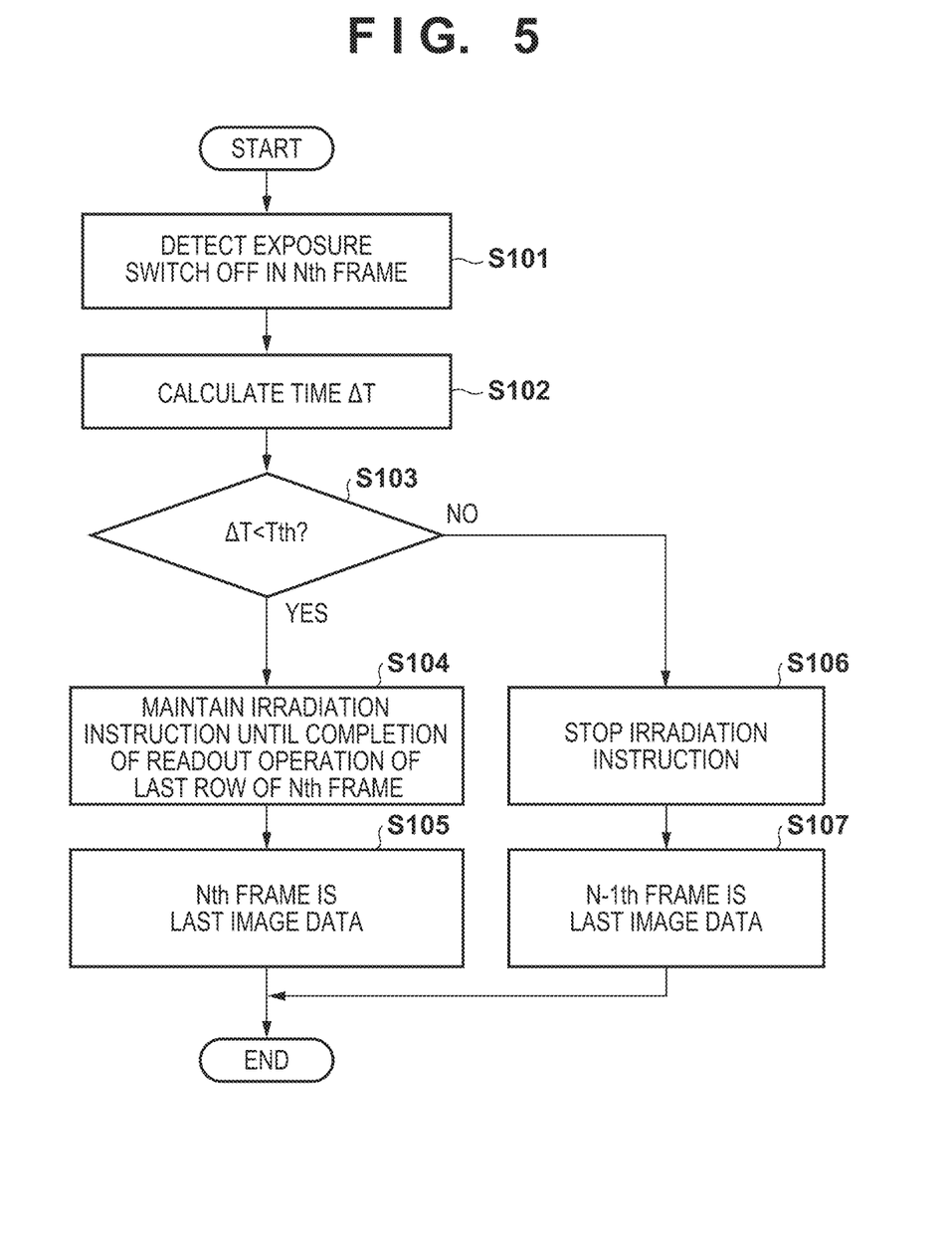
FIG. 5 is a flowchart for explaining a method of selecting a continuous fluoroscopy terminating operation of the radiation imaging system shown in FIG. 1.

First, for example, when the user releases the exposure switch of the operation UI 302 in the Nth frame, the controller 101 of the radiation imaging apparatus 100 detects (recognizes) turn-off of the exposure switch (step S101). At this time, the controller 101 uses, for example, the timer 113 to obtain a time Toff from the completion of the readout operation 510 of the last row (Nth row) in the immediately preceding (N−1)th frame to the detection of the turn-off of the exposure switch. Then, the controller 101 obtains a time $\Delta T$ from the turn-off of the exposure switch to the completion of the readout operation 510 of the last row in the Nth frame. For example, by using a time Tcyc of one cycle of a frame for the continuous fluoroscopy imaging mode currently in operation, the time $\Delta T$ until the completion of the readout operation 510 of the last row in the Nth frame can be calculated as $\Delta T = Tcyc - Toff$ (step S102).

Then, the controller 101 determines whether the time $\Delta T$ is smaller than a predetermined threshold value Tth (step S103). Here, if the time $\Delta T$ is smaller than the threshold value Tth (YES in step S103), the controller 101 operates so as to maintain the "irradiation instruction" signal at high level (irradiation) until the completion of the readout operation 510 of the last row (Nth row) in the Nth frame as shown in FIG. 3 (step S104). Further, the control apparatus 400 causes the display unit 406 to display an image based on the last image data generated by the generation operation in the Nth frame during which it was instructed to terminate the radiation irradiation (step S105).

On the other hand, if the time $\Delta T$ is equal to or larger than the threshold value Tth (NO in step S103), if the "irradiation instruction" signal is maintained at high level until the completion of the readout operation 510 of the last row (Nth row) in the Nth frame, the radiation irradiation is performed for a predetermined period or more even though the exposure switch has been released. Particularly, when the frame rate for the continuous fluoroscopy imaging mode in operation is low, this leads to a long radiation irradiation time after the turn-off of the exposure switch. In such a case, as shown in FIG. 4, in accordance with the user instruction to terminate the radiation irradiation, the "irradiation instruction" signal is immediately changed to low level to stop the radiation irradiation (step S106). Further, the control apparatus 400 causes the display unit 406 to display an image based on the image data (last image data) generated by the generation operation in the (N−1)th frame one before the generation operation in the Nth frame during which it was instructed to terminate the radiation irradiation (step S107). In this manner, in accordance with the timing of the release of the exposure switch, it is possible to select the appropriate continuous fluoroscopy terminating operation without excessive continuation of the radiation irradiation after the release of the exposure switch to terminate the radiation irradiation.

The method of selecting the continuous fluoroscopy terminating operation is not limited to the method described above. For example, the terminating operation may be uniquely determined in accordance with the frame rate of the generation operation for the used continuous fluoroscopy imaging mode. For example, if the frame rate is equal to or higher than a predetermined frame rate, the controller 101 may control so as to continue the "irradiation instruction" signal until the completion of the readout operation 510 of the last row in the Nth frame as shown in FIG. 3. If the frame rate is lower than the predetermined frame rate, since the period from the release of the exposure switch to the stop of the radiation irradiation may become long, the controller 101 may control so as to immediately stop the "irradiation instruction" signal as shown in FIG. 4. By controlling as described above, in accordance with the frame rate for the used continuous fluoroscopy imaging mode, it is possible to select the appropriate continuous fluoroscopy terminating operation without excessive continuation of the radiation irradiation after the release of the exposure switch. Here, the frame rate is defined by the generation operation (the accumulating operation 500 and the readout operation 510) to be performed on each row. For example, the frame rate can be the number of the generation operations to be performed on one row in a predetermined time.

In the radiation imaging apparatus 100, imaging may be performed using not all the rows in the sensor array 204. Here, a continuous fluoroscopy terminating operation which is preformed when a predetermined region of interest (ROI) 702 in the sensor array 204 is designated as the region to be used for imaging will be described. In this embodiment, in accordance with the timing at which the user instructs, by releasing the exposure switch or the like, to terminate the radiation irradiation and the designated ROI 702, a period to maintain the "irradiation instruction" signal at high level upon terminating the continuous fluoroscopy is changed.

First, with reference to FIG. 6, an example of the image data readout direction in the sensor array 204 and the ROI 702 will be described. As has been described above, the controller 101 of the radiation imaging apparatus 100 controls the plurality of pixels 207 arranged in the sensor array 204 so as to perform the readout operation on a row basis. Here, as shown in FIG. 6, the image data readout operation is performed from the upper portion (first row) to the lower portion (Nth row) of the sensor array 204 in the direction indicated by an arrow 703.

Here, for example, the ROI 702 may indicate the effective region of an image defined in advance for each imaging mode, or may be individually defined as a region of interest set for each imaging procedure or each protocol. Alternatively, for the ROI 702, the radiation imaging apparatus 100 may obtain the stop information of a collimator connected to the radiation source 301, and the radiation irradiation range obtained from the stop information may be defined as the ROI 702. Here, a case in which the ROI 702 is set in the center of the sensor array 204 as shown in FIG. 6 will be taken as an example and described.

Figure 6:
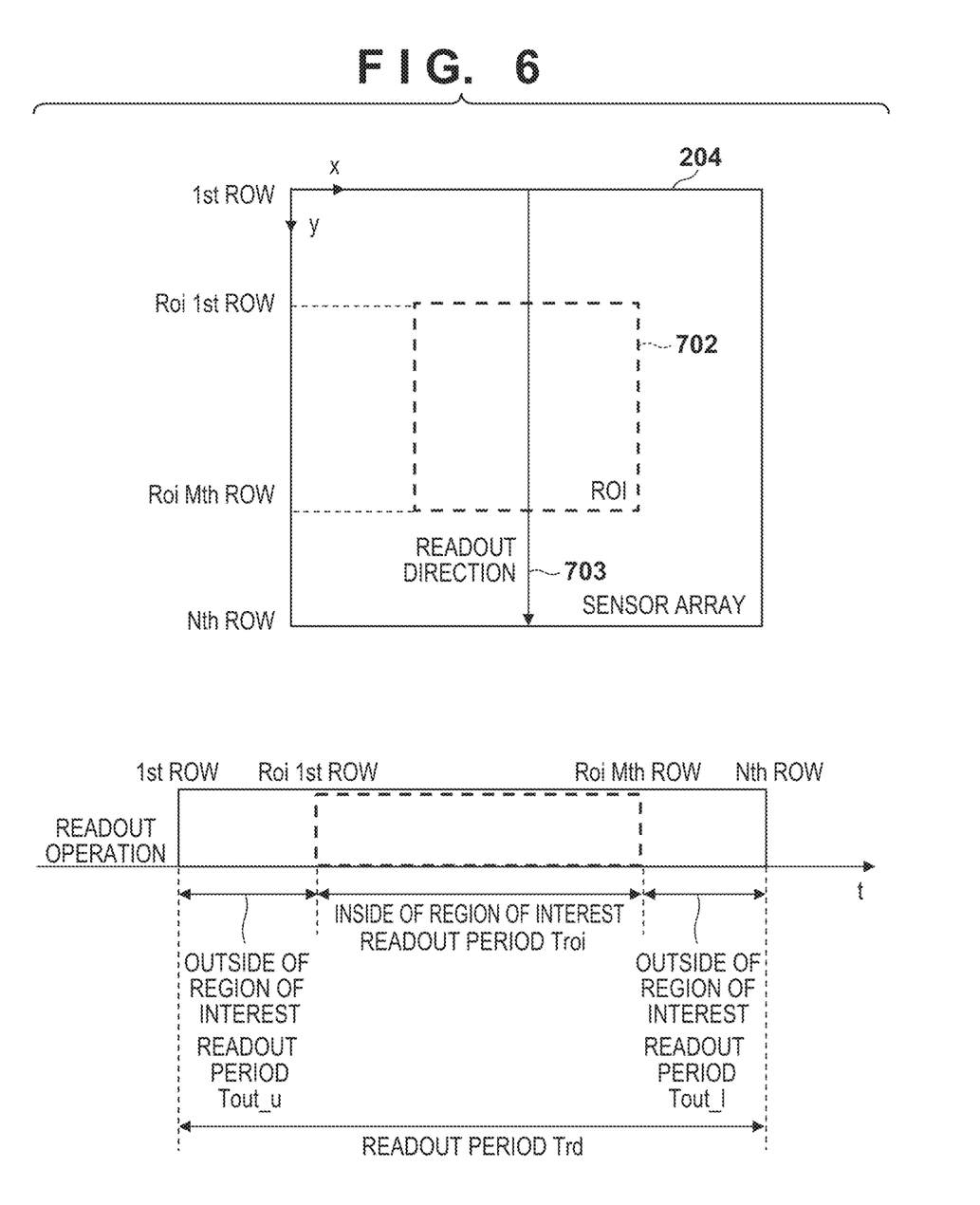
FIG. 6 is a view showing an example of an image readout direction and a region of interest in the radiation imaging system shown in FIG. 1.

As shown in FIG. 6, a readout period Trd of reading out image data from the respective pixels 207 in the sensor array 204 for each row includes a readout period Tout_u for image data from the first row to the (Roi1−1)th row outside the region of interest, a readout period Troi for image data in the ROI 702 (from the (Roi1)th row to the (RoiM)th row), and a readout period Tout_1 for image data from the (RoiM+1)th row to the Nth row outside the region of interest. An example of the operation timing control during continuous fluoroscopy performed when the ROI 702 is set as shown in FIG. 6 will be described with reference to FIG. 7. The operation upon starting continuous fluoroscopy may be similar to that shown in FIG. 3, so that the description thereof will be omitted here.

Figure 7:
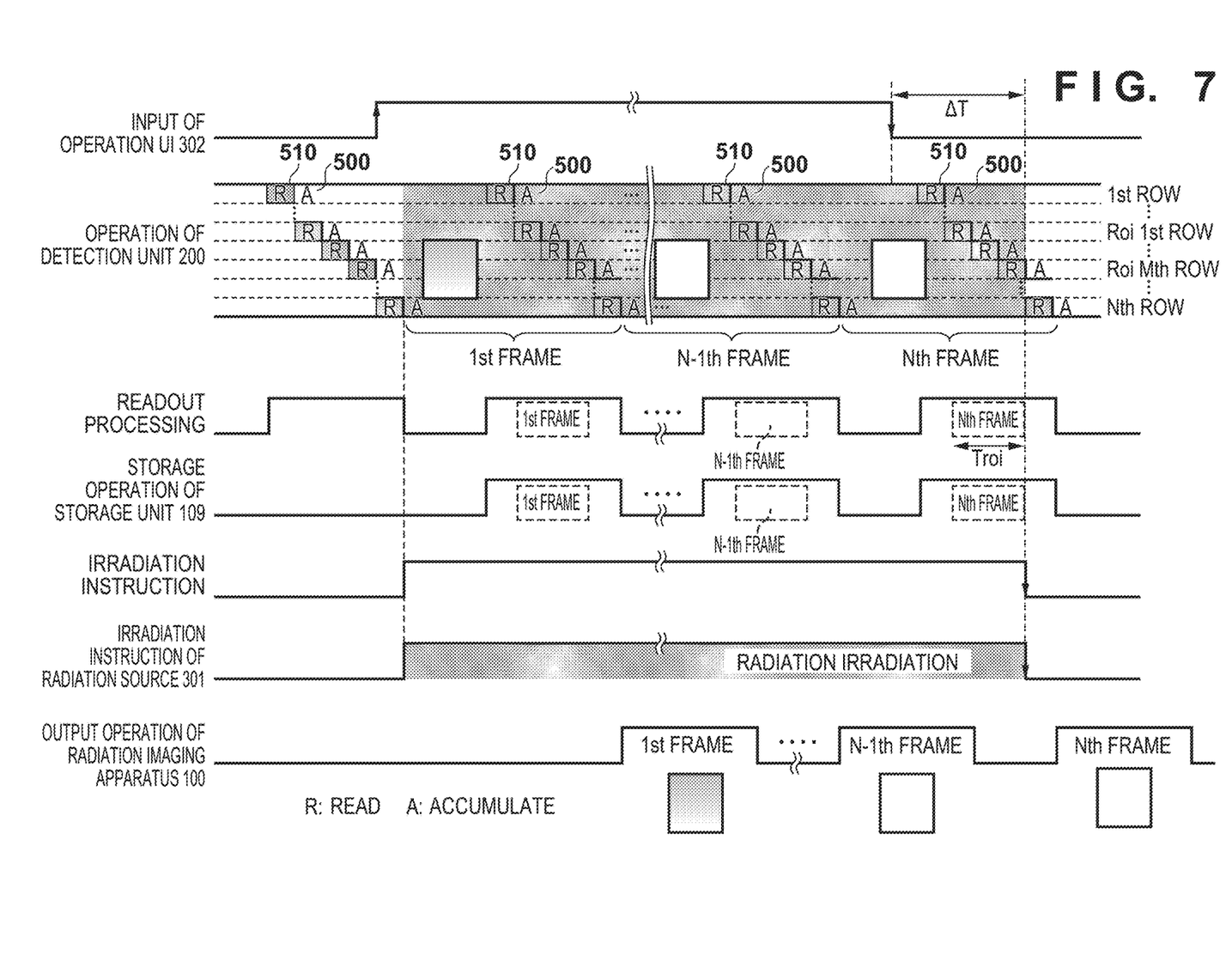
FIG. 7 is a timing chart for explaining still another operation of the radiation imaging system shown in FIG. 1.

A case will be described in which continuous fluoroscopy is interrupted or terminated by the user returning the exposure switch of the operation UT 302 in the Nth frame. When it is instructed to terminate the radiation irradiation, the irradiation timing controller 114 maintains the "irradiation instruction" signal at high level until the timing at which the readout operation 510 of the last row ((RoiM)th row) in the ROI 702 is completed in the Nth frame in which the accumulating operation 500 has been already started. When the readout operations 510 of all the rows in the ROI 702 in the Nth frame are completed, the irradiation timing controller 114 changes the "irradiation instruction" signal to low level to stop the radiation irradiation.

Thus, since the radiation irradiation is performed until the accumulating operation and the readout operation of the last row in the ROI 702 in the generation operation in the Nth frame are completed, the image data for the Nth frame during which it was instructed to terminate the radiation irradiation is data of the time at which the radiation irradiation times are equal to each other for the respective rows at least in the ROI 702. The control apparatus 400 causes the display unit 406 to display an image based on the last image data generated by the generation operation in the Nth frame during which it was instructed to terminate the radiation irradiation. Thus, it is possible to provide the radiation imaging system SYS that can obtain, even when the continuous fluoroscopy is terminated or interrupted, a clear image in which each pixel 207 at least in the ROI 702 is irradiated with radiation.

Further, a case will be described in which the exposure switch is released between the (RoiM+1)th row and the Nth row (the period Tout_1 shown in FIG. 6) during the readout operation in the (N−1)th frame shown in FIG. 7. In this case, since the readout operation 510 of the last row ((RoiM)th row) in the ROI 702 in the (N−1)th frame is already completed, the irradiation timing controller 114 maintains the "irradiation instruction" signal at high level until the readout operation 510 of the last row ((RoiM)th row) in the ROI 702 in the next Nth frame is completed. When the readout operations 510 of all the rows in the ROI 702 in the Nth frame are completed, the irradiation timing controller 114 changes the "irradiation instruction" signal to low level to stop the radiation irradiation. Thus, the irradiation instruction may be continued until the timing of the completion of the readout operation 510 of the last row ((RoiM)th row) in the ROI 702 in the next frame after the exposure switch is released.

The operation shown in FIG. 7 shows that the accumulating operation 500 and the readout operation 510 are performed row by row from the first row to the Nth row (last row), but the present invention is not limited to this. For example, the accumulating operation 500 and the readout operation 510 may be performed for multiple rows such as for two rows or for three rows. Further, the radiation source 301 stops the radiation irradiation in accordance with the completion of the accumulating operation 500 and the readout operation 510 of the last row ((RoiM)th row) in the ROI 702 in the generation operation in the Nth frame, but the present invention is not limited to this. The radiation source 301 may stop the radiation irradiation in accordance with the completion of the accumulating operation 500 of the last row ((RoiM)th row) in the ROI 702 in the generation operation in the Nth frame. Even in this case, the radiation irradiation times in the accumulating operations 500 can be equal to each other for the respective rows in the ROI 702.

In the region from the (RoiM+1)th row to the Nth row outside the ROI 702, the radiation irradiation time in the accumulating operation 500 changes for each row. Therefore, in the image generated in the Nth frame, shading can occur in the region outside the ROI 702. However, since this is not the image data of the region used for observation, diagnosis, or the like, a problem is unlikely to occur in observation, diagnosis, or the like using the obtained image.

After it is instructed to terminate the radiation irradiation, the control apparatus 400 causes the radiation imaging apparatus 100 to stop the generation operation in which the accumulating operation 500 and the readout operation 510 are performed. In this case, the control apparatus 400 may not cause the radiation imaging apparatus 100 to output, to the control apparatus 400, the image data generated by the generation operation performed after the generation operation in which the last image data was generated. Alternatively, in this case, the image data generated by the generation operation performed after the generation operation in which the last image data was generated may not be transferred from the detection unit 200 to the controller 101. Alternatively, for example, the image data generated by the generation operation performed after the generation operation in which the last image data was generated may not be stored in the storage unit 109. Since the image data generated by the generation operation performed after the generation operation in which the last image data was generated is not transferred to the storage unit 109 or the communication unit 112, it is not output from the radiation imaging apparatus 100. These operations may be similar to the operations described above with reference to FIG. 3.

For example, the image displayed on the display unit 406 after the radiation irradiation is terminated is not limited to an image based on the last image data alone. An image based on a plurality of image data may be displayed. This operation may be similar to the operation described above with reference to FIG. 3.

Also in the continuous fluoroscopy for which the predetermined region of interest (ROI) 702 in the sensor array 204 is designated as the region used for imaging, it is possible to perform the continuous fluoroscopy terminating operation as shown in FIG. 4 described above. The operation in this case is similar to the operation shown in FIG. 4. When an instruction to terminate the radiation irradiation is input, the irradiation timing controller 114 changes the "irradiation instruction" signal to low level to stop the radiation irradiation.

When the exposure switch is released, the radiation imaging apparatus 100 may determine whether to extend the radiation irradiation by maintaining the "irradiation instruction" signal until the completion of the readout operation 510 of the last row ((RoiM)th row) in the ROI 702 in the Nth frame as shown in FIG. 7, or to immediately stop the radiation irradiation as shown in FIG. 4, and switch the terminating operation. An example of the terminating operation determination procedure in the continuous fluoroscopy in this case will be described with reference to FIG. 8.

Figure 8:
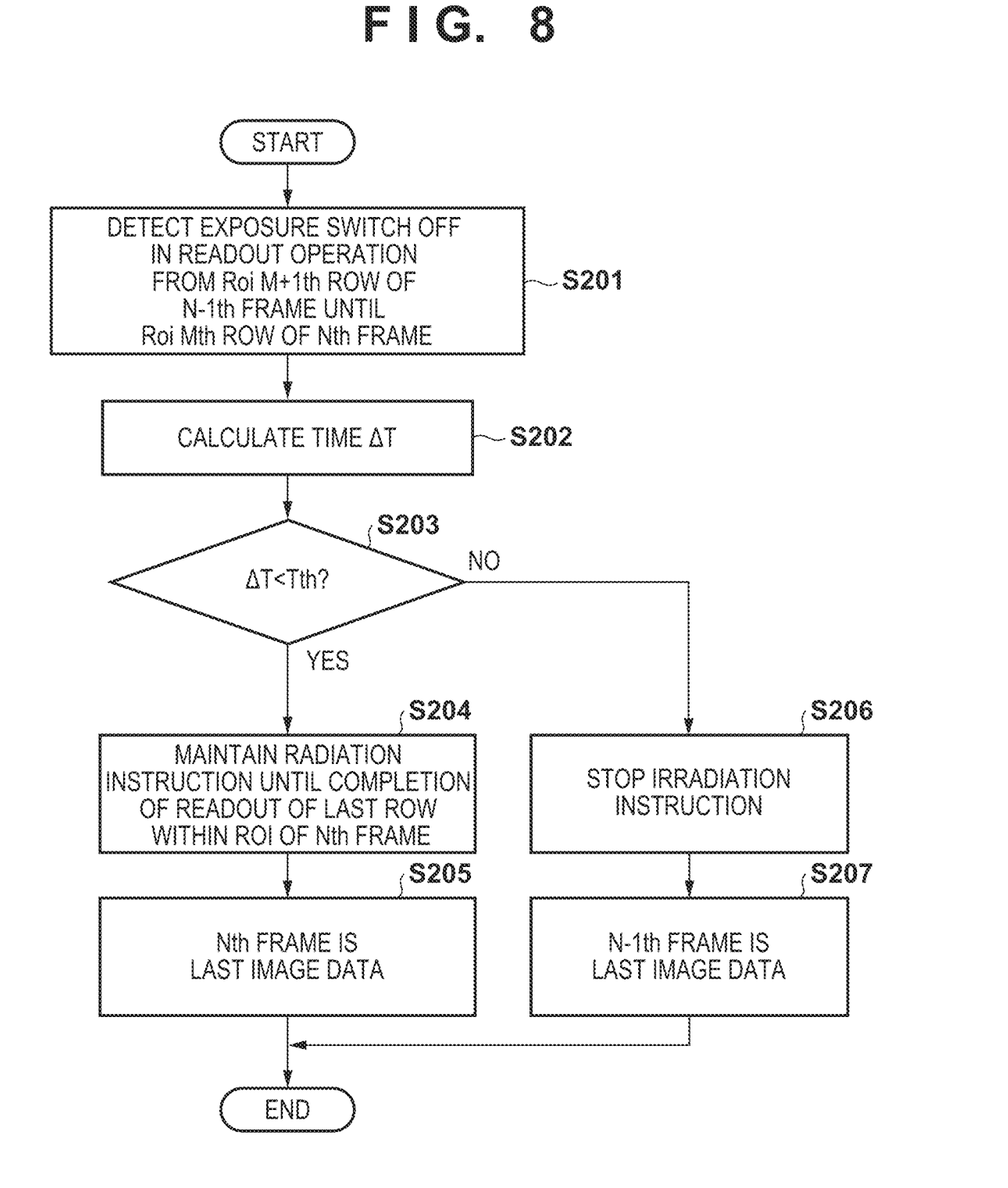
FIG. 8 is a flowchart for explaining another method of selecting the continuous fluoroscopy terminating operation of the radiation imaging system shown in FIG. 1.

First, for example, when the user releases the exposure switch of the operation UI 302 in a period from the completion of the readout operation 510 of the last row ((RoiM)th row) in the ROI 702 (the start of the readout operation 510 of the (RoiM+1)th row) in the (N−1)th frame to the readout operation 510 of the last row ((RoiM)th row) in the ROI 702 in the Nth frame, the controller 101 of the radiation imaging apparatus detects turn-off of the exposure switch (step S201). At this time, the controller 101 uses, for example, the timer 113 to obtain the time Toff from the completion of the readout operation 510 of the last row ((RoiM)th row) in the ROI 702 in the immediately preceding (N−1)th frame to the detection of the turn-off of the exposure switch. Then, the controller 101 obtains the time ΔT from the turn-off of the exposure switch to the completion of the readout operation 510 of the last row ((RoiM)th row) in the ROI 702 in the Nth frame. For example, by using the time Tcyc of one cycle of a frame for the continuous fluoroscopy imaging mode currently in operation, the time ΔT from the turn-off of the exposure switch to the completion of the readout operation 510 of the last row ((RoiM)th row) in the ROI 702 in the Nth frame can be calculated as ΔT=Tcyc−Toff (step S202).

Then, the controller 101 determines whether the time ΔT is smaller than the predetermined threshold value Tth (step S203). Here, if the time ΔT is smaller than the threshold value Tth (YES in step S203), the controller 101 operates so as to maintain the "irradiation instruction" signal at high level (irradiation) until the completion of the readout operation 510 of the last row ((RoiM)th row) in the ROI 702 in the Nth frame as shown in FIG. 7 (step S204). Further, the control apparatus 400 causes the display unit 406 to display an image based on the last image data generated by the generation operation in the Nth frame (step S205).

On the other hand, if the time ΔT is equal to or larger than the threshold value Tth (NO in step S203), as shown in FIG. 4, the irradiation timing controller 114 immediately changes the "irradiation instruction" signal to low level to stop the radiation irradiation (step S206). Further, the control apparatus 400 causes the display unit 406 to display an image based on the image data (last image data) generated by the generation operation in the (N−1)th frame one before the generation operation in the Nth frame during which it was instructed to terminate the radiation irradiation (step S207). In this manner, in accordance with the timing of the release of the exposure switch, it is possible to select the appropriate continuous fluoroscopy terminating operation without excessive continuation of the radiation irradiation after the release of the exposure switch to terminate the radiation irradiation.

The method of selecting the terminating operation during continuous fluoroscopy is not limited to the method described above. For example, the terminating operation may be uniquely determined in accordance with the frame rate of the generation operation for the used continuous fluoroscopy imaging mode. For example, if the frame rate is equal to or higher than a predetermined frame rate, the controller 101 may control so as to continue the "irradiation instruction" signal until the completion of the readout operation 510 of the last row ((RoiM)th row) in the ROI 702 in the Nth frame as shown in FIG. 7. If the frame rate is lower than the predetermined frame rate, since the period from the release of the exposure switch to the stop of the radiation irradiation may become long, the controller 101 may control so as to immediately stop the "irradiation instruction" signal as shown in FIG. 4. By controlling as described above, in accordance with the frame rate for the used continuous fluoroscopy imaging mode, it is possible to select the continuous fluoroscopy terminating operation with which occurrence of shading in the image at least in the ROI 702 is suppressed without excessive continuation of the radiation irradiation after the release of the exposure switch.

In this embodiment, it has been described that the ROI 702 is set in the center of the sensor array 204 as shown in FIG. 6. However, the preset invention is not limited to this, and similar control can be applied to the ROI 702 set in an arbitrary location.

As has been described above, in the radiation imaging system SYS having the last image hold function, an image to be displayed on the display unit 406 when fluoroscopic imaging is interrupted is generated from image data in which the radiation irradiation times in the accumulating operations 500 are equal to each other for the respective rows. Thus, shading in the image displayed when fluoroscopic imaging is interrupted is suppressed, so that the image quality improves and the more user-friendly radiation imaging system SYS can be implemented.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-021262, filed Feb. 12, 2021, and Japanese Patent Application No. 2021-198700, filed Dec. 7, 2021 which are hereby incorporated by reference herein in their entirety.

What is claimed is:

1. A radiation imaging system, comprising:
a radiation imaging apparatus having a sensor panel in which a plurality of pixels are arranged in a matrix configured to acquire a radiation image;
a radiation irradiation apparatus configured to irradiate radiation from a radiation source; and
one or more controllers configured to control an operation of the radiation imaging apparatus, wherein
said one or more controllers are configured (i) to sequentially acquire a plurality of radiation images in a state where radiation is continuously irradiated from the radiation source, wherein image signals required to acquire one radiation image are read from the plurality of pixels row by row, and (ii) after a user instruction to terminate radiation irradiation by the radiation source is detected, to wait until reading of image signals from pixels of the predetermined row is completed, and execute a communication processing for stopping the irradiation by the irradiation apparatus based on the completion of the reading of image signals from the pixels in the predetermined row.

2. A radiation imaging system, comprising:
a radiation imaging apparatus having a sensor panel in which a plurality of pixels are arranged in a matrix configured to acquire a radiation image;
a radiation irradiation apparatus configured to irradiate radiation from a radiation source;
an information processing apparatus configured to cause a display device to display information; and
one or more controllers configured to control an operation of the radiation imaging apparatus, wherein
said one or more controllers are configured (i) to sequentially acquire a plurality of radiation images in a state where radiation is continuously irradiated from the radiation source, wherein image signals required to acquire one radiation image are read from the plurality of pixels row by row, and (ii) transmit first radiation image to the information processing apparatus via a network in accordance with the completion of reading of image signals required to acquire the first radiation image, and continue until acquisition of image signals required to acquire second radiation image is completed according to detection of user instruction to terminate radiation irradiation by the radiation source during the reading of the image signals required to acquire the second radiation image following the first radiation image, and not transmit the second radiation image to the information processing apparatus via the network.

3. The system according to claim 1, further comprising a control apparatus configured to control the system, wherein
the radiation imaging apparatus comprises a driving controller configured to control the sensor panel, and an irradiation timing controller configured to output a signal instructing the radiation source to perform radiation irradiation,
the control apparatus comprises an imaging controller configured to control the radiation imaging apparatus, and an irradiation controller configured to control an irradiation condition of radiation applied from the radiation source, and
the one or more controllers include the driving controller, the irradiation timing controller, the imaging controller, and the irradiation controller.

4. The system according to claim 3, wherein during radiation irradiation, the one or more controllers are configured to cause the radiation imaging apparatus to repeat a generation operation of generating one image data by causing the plurality of pixels to perform an accumulating operation and a readout operation, and
the one or more controllers are configured to (i) cause the radiation imaging apparatus to stop the generation operation after it is instructed to terminate the radiation irradiation, and (ii) cause the sensor panel not to output image data generated by, among the generation operations, the generation operation performed after the generation operation in which the last image data was generated.

5. The system according to claim 1, wherein during radiation irradiation, the one or more controllers are configured to cause the radiation imaging apparatus to repeat a generation operation of generating one image data by causing the plurality of pixels to perform an accumulating operation and a readout operation, and
the one of more controllers are configured to (i) cause the radiation imaging apparatus to stop the generation operation after it is instructed to terminate radiation irradiation, and (ii) cause the radiation imaging apparatus not to output image data generated by, among the generation operations, the generation operation performed after the generation operation in which the last image data was generated.

6. The system according to claim 1, wherein during radiation irradiation, the one or more controllers are configured to cause the radiation imaging apparatus to repeat a generation operation of generating one image data by causing the plurality of pixels to perform an accumulating operation and a readout operation, and
the one or more controllers are configured to (i) cause the radiation imaging apparatus to start the generation operation before it is instructed to start the radiation irradiation, and (ii) when it is instructed to start the radiation irradiation, cause the radiation source to start the radiation irradiation in accordance with completion of the readout operation of the predetermined row in, among the generation operations, the generation operation during which it was instructed to start the radiation irradiation.

7. The system according to claim 1, further comprising an information processing apparatus configured to cause a display device to display information, wherein
during radiation irradiation, the one or more controllers are configured to causes the radiation imaging apparatus to repeat a generation operation of generating one image data by causing the plurality of pixels to perform an accumulating operation and a readout operation, and
the information processing apparatus is configured to cause the display device to display an image based on a plurality of image data including the last image data and image data generated by, among the generation operations, the generation operation immediately preceding the generation operation in which the last image data was generated.

8. The system according to claim 1, wherein the predetermined row is last row of the matrix.

9. The system according to claim 1, wherein the sensor panel has a plurality of regions of interest, and
the predetermined row is last row of selected region selected from the plurality of regions of interest.

10. A radiation imaging system, comprising:
a radiation imaging apparatus having a sensor panel in which a plurality of pixels are arranged in a matrix configured to acquire a radiation image;
a radiation irradiation apparatus configured to irradiate radiation from a radiation source;
an information processing apparatus configured to cause a display device to display information; and
one or more controllers configured to control an operation of the radiation imaging apparatus, wherein
said one or more controllers are configured (i) to sequentially acquire a plurality of radiation images in a state where radiation is continuously irradiated from the radiation source, wherein image signals required to acquire one radiation image are read from the plurality of pixels row by row; and (ii) cause the radiation imaging apparatus to operate by selecting one of (a) a first terminating operation configured, after a user instruction to terminate radiation irradiation by the radiation source is detected, to be put on hold until a timing of completion of reading of image signals from pixels of the predetermined row, and execute communication processing for stopping irradiation by the irradiation apparatus based on the completion of the reading of the image signals from the pixels in the predetermined row, and (b) a second terminating operation configured transmit first radiation image to the information processing apparatus via a network in accordance with the completion of reading of image signals required to acquire the first radiation image, and continue until acquisition of image signals required to acquire second radiation image is completed according to detection of user instruction to terminate radiation irradiation by the radiation source during the reading of the image signals required to acquire the second radiation image following the first radiation image, and not transmit the second radiation image to the information processing apparatus via the network.

11. The system according to claim 10, wherein during radiation irradiation, the one or more controllers are configured to cause the radiation imaging apparatus to repeat a generation operation of generating one image data by causing the plurality of pixels to perform an accumulating operation and a readout operation, and
selection of one of the first terminating operation and the second terminating operation depends on a time from the instruction to terminate radiation irradiation to completion of the accumulating operation and the readout operation of the predetermined row in, among the generation operations, the next generation operation of the generation operation during which it was instructed to terminate the radiation irradiation.

12. The system according to claim 10, wherein during radiation irradiation, the one or more controllers are configured to cause the radiation imaging apparatus to repeat a generation operation of generating one image data by causing the plurality of pixels to perform an accumulating operation and a readout operation, and
selection of one of the first terminating operation and the second terminating operation depends on a frame rate of the generation operation.

13. The system according to claim 10, wherein the predetermined row is last row of the matrix.

14. The system according to claim 10, wherein the sensor panel has a plurality of regions of interest, and
the predetermined row is last row of selected region selected from the plurality of regions of interest.

* * * * *